United States Patent [19]

Aboul-Hosn

[11] Patent Number: 5,741,234

[45] Date of Patent: Apr. 21, 1998

[54] ANATOMICAL CAVITY ACCESS SEALING CONDIT

[76] Inventor: Walid Nagib Aboul-Hosn, 3462 Bridgeford Dr., Sacramento, Calif. 95834

[21] Appl. No.: 680,929

[22] Filed: Jul. 16, 1996

[51] Int. Cl.[6] .................................................. A61B 17/34
[52] U.S. Cl. ........................... 604/174; 604/175; 604/178
[58] Field of Search ...................................... 604/167, 165, 604/174, 178, 104, 105, 106, 107

[56] References Cited

U.S. PATENT DOCUMENTS

| | | | |
|---|---|---|---|
| 2,899,960 | 8/1959 | Ginsberg | 128/221 |
| 3,783,454 | 1/1974 | Sausse et al. | 128/334 |
| 4,516,578 | 5/1985 | Shuffield | 604/104 |
| 4,642,101 | 2/1987 | Krolikowski et al. | 604/164 |
| 5,122,122 | 6/1992 | Allgood | 604/174 |
| 5,176,697 | 1/1993 | Hasson | 604/191 |
| 5,234,455 | 8/1993 | Mulhollan | 606/191 |
| 5,250,058 | 10/1993 | Miller et al. | 606/154 |
| 5,358,488 | 10/1994 | Suriyapa | 604/96 |
| 5,456,714 | 10/1995 | Owen | 623/1 |

*Primary Examiner*—Sam Rimell
*Assistant Examiner*—Luke Yeh
*Attorney, Agent, or Firm*—Wilson Sonsini Goodrich & Rosati

[57] ABSTRACT

A sealing conduit for use with a portal formed on the body which enable surgical, diagnostic and assistive instruments to be inserted into the body during least invasive medical procedures. The sealing conduit includes an elongated cylindrical member with a continuous central lumen therebetween. A flexible annular lip structure is attached or formed on the inside surface of the cylindrical member which is folded in a retracted position inside the cylindrical member or extended through the distal opening thereof. During use, a penetrating member is disposed inside the cylindrical member which is moved downward to forcibly move the annular lip structure from the retracted to the extended position. When the annular lip structure is in the extended position, distal end of the sealing conduit is located just inside the desired vessel or conduit and outward migration of the sealing conduit through the portal is prevented. An upper flexible ring is disposed around the cylindrical member which is moved by downward thereon by a plurality of suture lines. When the suture lines are pulled, the annular lip structure and flexible ring are squeezed together to securely hold and create a seal around the portal.

6 Claims, 6 Drawing Sheets

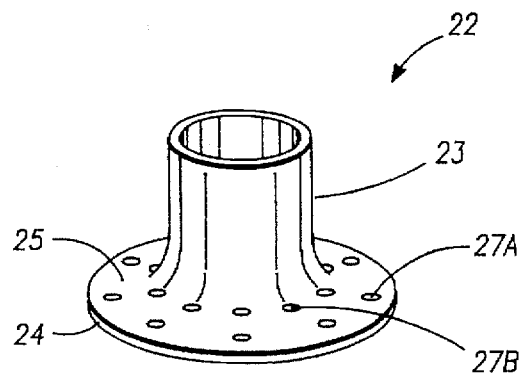
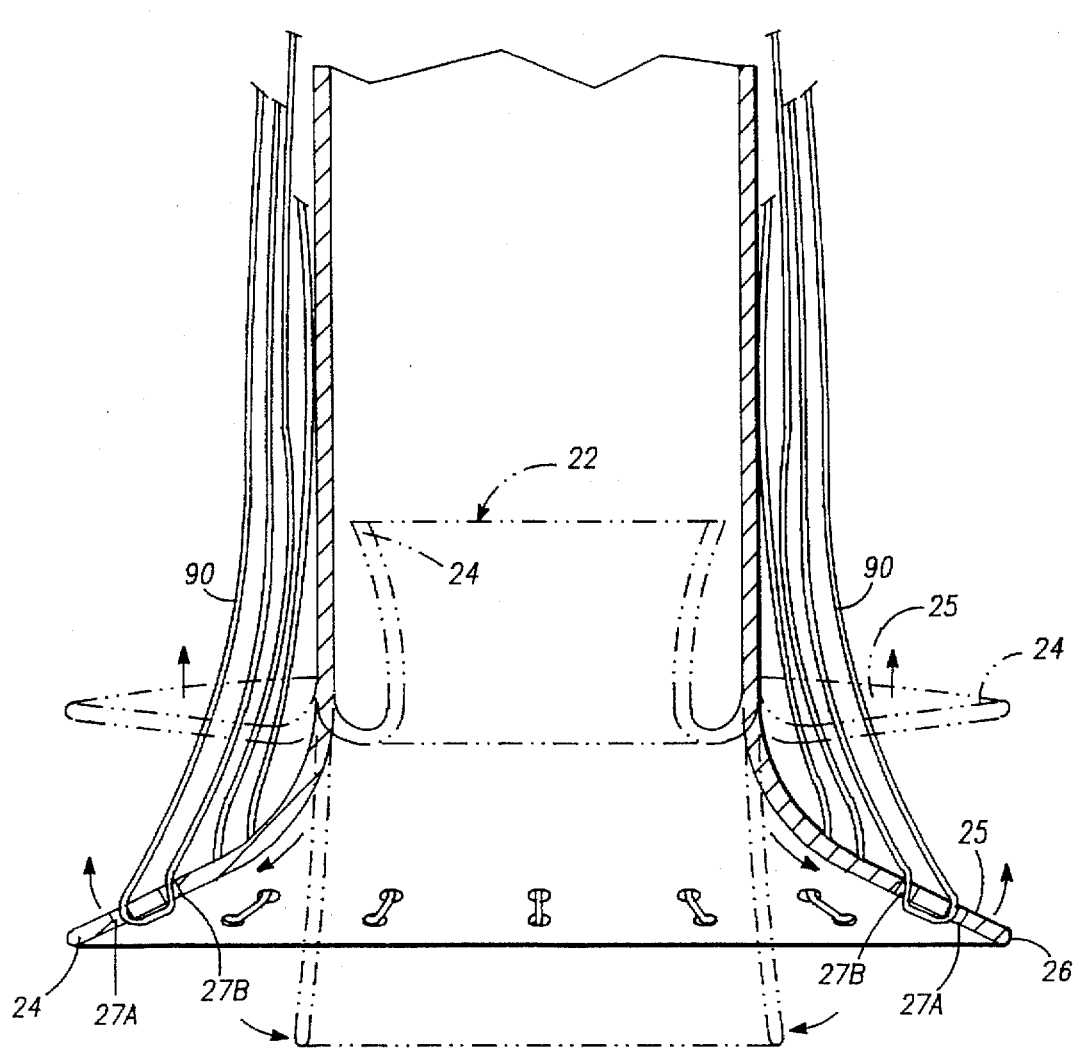
FIG.-4
FIG.-5

ANATOMICAL CAVITY ACCESS SEALING CONDIT

BACKGROUND OF THE INVENTION

1. Field of Invention

This invention relates to anatomical cavity access conduits and more specifically, to such conduits which include means for attaching and sealing them to an anatomical cavity or vessel wall.

2. Description of the Related Art

Conduits are widely used in medical procedures to gain access to various blood vessels, spaces, cavities, and organs in the human body. Such conduits are used to provide direct, limited access to a desired area in the body in which a medical procedure is to be conducted. Such procedures, known as least invasive procedures, require a small portal to be created through the skin, underlying soft tissue, and the walls of the cavity, space, or organ so that instruments used in a medical procedure may be introduced.

Least invasive procedures offer many advantages over open, major surgical procedures. Such advantages include minimal invasiveness and trauma, reduced hospitalization and rehabilitation times, performance of surgery on an outpatient basis, decreased patient discomfort, enhanced post-surgical and diagnostic mobility and more cosmetically pleasing wounds. In addition to these advantages, conduits themselves serve an important functional role by providing a smooth pathway for instruments used in the medical procedure to be inserted and removed from the portal.

In many least invasive procedures, such as transluminal angioplasty or angiography procedures, portals are formed far and remote from the operating site. Typically, these portals are formed in the skin and underlying soft tissue adjacent to the groin or shoulder which provide access to a relatively large artery, such as the femoral or subclavian arteries which leads to the desired operating site. One reason for accessing a cavity, space or organ through a remote portal, is the inability of the conduit used in the prior art to directly access the sides of the cavity, space or organ. Ideally, the conduit should provide direct access to the operating site with minimal bleeding, minimal contamination, and easy removal.

Structurally, the inside diameter of the conduit must be sufficient so that various instruments can be easily inserted and removed therefrom. Generally, the greater the distance between the operating site and the portal site, the more complex the instrument must be to perform the required surgery. For example, instruments used for cardiac surgery must be placed on the tip of a long catheter that must be snaked to the operating site. In order to do so, a multitude of devices must be used to track and control the catheter along it's path.

Unfortunately, one important size limitation of a conduit is the size of the blood vessel or cavity accessed by the conduit. Generally, the outer diameter of a conduit is limited by the inside diameter of the accessed blood vessel or cavity. Since the inside diameter of the conduit is limited by the conduit's outer diameter, the size and shape of the instruments inserted through the conduit are limited by the inside diameter of the conduit. Due to these size limitations, many instruments cannot be sufficiently miniaturized to be inserted through the conduit.

One important limitation of a conduit in the prior art is that it often falls out or protrudes excessively through the portal during use. Not only is this a great inconvenience to the surgeon, but can also cause damage to the underlying blood vessel or organ or occlude the flow of fluid therethrough. Generally, when inserting a conduit through a portal, it is desirable to dispose the conduit through the portal so that the conduit's distal end is just inside the blood vessel or organ in close proximity to the nearest side wall. Typically, sutures or a clamp is used to hold the conduit in place and prevent either its inward or outward movement through the portal. Unfortunately, these methods often fail. An improved means for securely attaching the conduit to the side walls of the portal, blood vessel or organ to prevent migration of the conduit through the portal is therefore needed.

SUMMARY OF THE INVENTION

It is a primary object of the present invention to provide a conduit that provides a seal around the portal to maintain adequate hemostasis and minimal contamination during use.

It is another object of the present invention to provide such a conduit that can be easily and properly inserted into a desired blood vessel or cavity without occluding the blood vessel or cavity.

It is a further object of the invention to provide such a conduit that can be temporarily attached to the side walls of portal to prevent the inward and outward migration of the conduit through the portal during use.

These and other objects of the invention which will become apparent are met by providing a sealing conduit which includes an elongated cylindrical member designed to be inserted through a portal of minimal size formed in anatomical tissue. The cylindrical member is opened at its opposite distal and proximal ends and has an elongated penetrating member disposed therein designed to move longitudinally inside the cylindrical member during use. The cylindrical member has a conical-shaped housing attached at its proximal end which acts as a handling implement for inserting and removing the sealing conduit from the portal. Located inside the housing is an optional valve assembly which selectively closes the upper end of the cylindrical member to prevent contaminates from outside the body from entering the portal during use. The size of the valve assembly can be adjusted to accommodate different size instruments inserted through the sealing conduit.

Attached or integrally formed on the inside surface, near the distal end of the cylindrical member is a flexible, annular lip structure. During assembly, the annular lip structure is folded into a retracted position inside the cylindrical member. When the cylindrical member is properly positioned through the portal, the outer edge of the annular lip structure is forcibly moved through the distal end of the cylindrical member thereby enabling the annular lip structure to unfold into an extended position from the distal end of the cylindrical member, as discussed below.

Disposed longitudinally inside the cylindrical member, is a penetrating member which is used to provide support and plug the cylindrical member when the cylindrical member is initially inserted into a blood vessel or cavity, and to facilitate the penetration of the conduit through the portal and underlying tissue or vessels. The penetrating member can also be used to force the annular lip structure through the distal end of the cylindrical member. In one embodiment shown and described below, the penetrating member has a relieved section in which the folded portion of the annular lip structure resides when the penetrating member is initially disposed into the cylindrical member. When the penetrating member is moved longitudinally downward inside the cylindrical member, the relieved section moves downward inside the cylindrical member thereby forcing the outer edge of the annular lip structure through the distal opening of the cylindrical member. When the annular lip structure is extended from the distal end of the cylindrical member, it automatically unfolds and extends outward from the cylindrical member. The location of the annular lip structure near the distal end of the cylindrical member positions the conduit immediately against the inside surface of the blood vessel or cavity so that fluid flowing through the blood vessel or cavity is not occluded. The annular lip structure is also sufficiently flexible so that when the cylindrical member is pulled outward through the portal when removing the sealing conduit therefrom, the annular lip structure bends inward.

When the sealing conduit is properly positioned through the portal and the annular lip structure is extended from the cylindrical member, a moving means is used to forcibly position the upper surface of the annular lip structure against the inside surface of the surrounding tissue located immediately adjacent to the portal. The portal is substantially smaller than the outer diameter of the annular lip structure so that when the annular lip structure is extended, it prevents the outward movement of the cylindrical member through the portal.

Disposed around the cylindrical member is an upper sealing member. During use, the upper sealing member selectively moves downward over the cylindrical member. After the cylindrical member is inserted into the portal and the annular lip structure is extended from the distal end of the cylindrical member and forced against the inside surface of the portal's surrounding tissue, the moving means is then used to move the upper sealing member downward along the cylindrical member until the upper sealing member's lower surface is pressed tightly against the outside surface of the tissue surrounding the portal. The moving means is used to squeeze the upper sealing member and the annular lip structure together on opposite sides of the portal to form a tight seal therearound and to securely hold the sealing conduit in the portal. By tightly squeezing the upper sealing member and the annular lip structure together in this manner, appropriate hemostasis is achieved. The sealing conduit is then ready for use in a desired medical procedure. To remove the sealing conduit from the portal, the moving means is loosened so that the annular lip structure can fold downward in alignment with the cylindrical member's longitudinal axis.

BRIEF DESCRIPTION OF THE DRAWINGS

FIG. 4 is a perspective view of the annular lip structure.

FIG. 5 is a partial, sectional, side elevational view of another embodiment of the invention with the annular lip structure integrally formed on the end of the cylindrical element showing how the annular lip structure unfolds therefrom.

DESCRIPTION OF THE PREFERRED EMBODIMENTS

Figure 1:
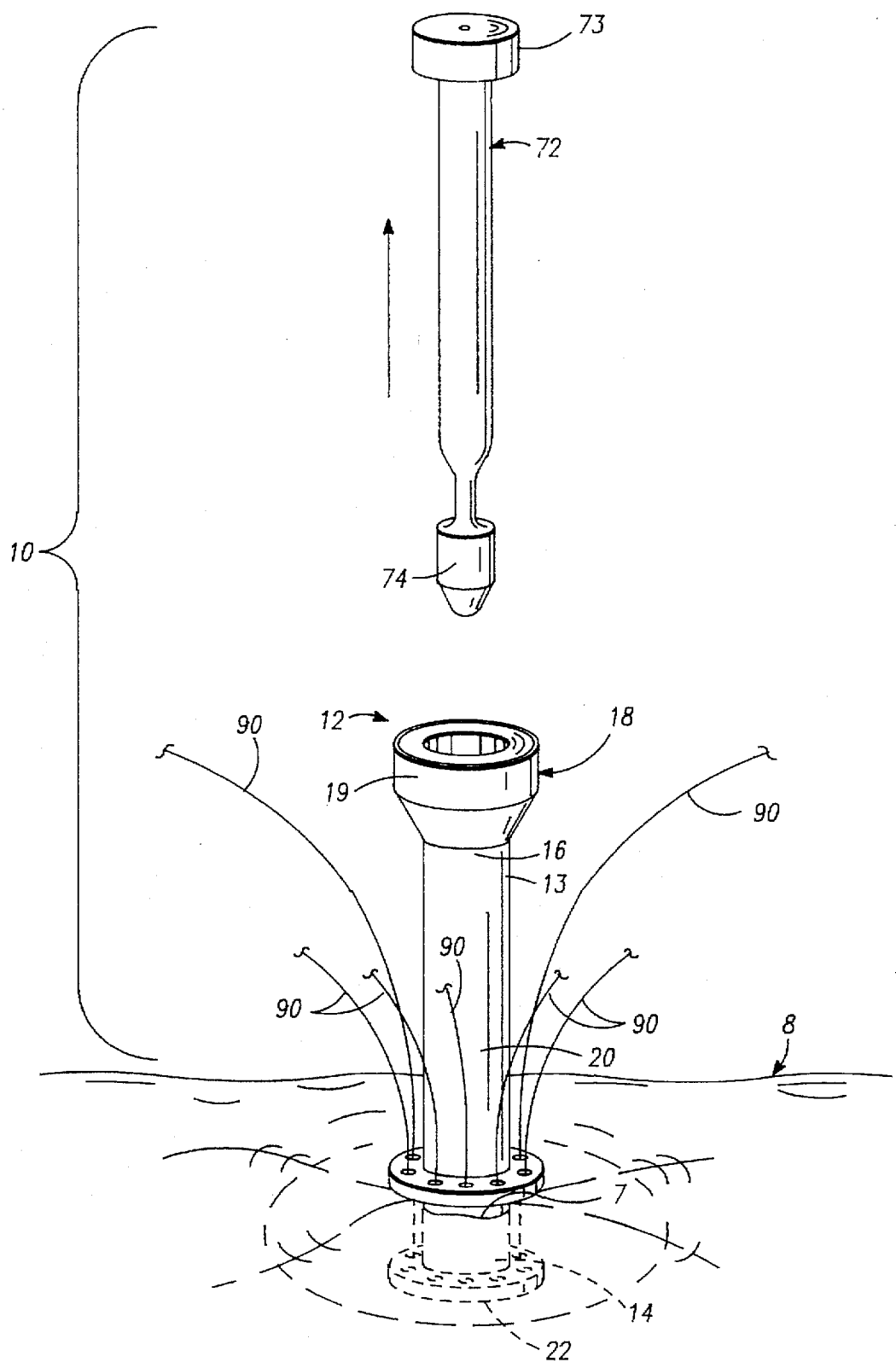
FIG. 1 is an exploded perspective view of the sealing conduit described herein inserted through a portal.

A sealing conduit, as indicated by reference number 10, is shown in the accompanying FIGS. 1–7, designed to be inserted through a minimal size portal 7 formed in desired tissue 8. The sealing conduit 10 is designed: (1) for proper placement in a desired blood vessel or cavity; (2) to form a seal around the portal 7 thereby preventing bleeding and the entry of contaminates therethrough; and, (3) to prevent undesirable inward and outward migration of the sealing conduit through the portal 7 during use.

More specifically, the sealing conduit 10 includes an elongated, cylindrical member 12 with opposite distal and proximal openings, 14, 16, respectively, with a continuous central lumen 20. In the embodiment shown, the cylindrical member 12 comprises an elongated cylindrical element 13 with an enlarged housing 18 formed or attached near its proximal opening 16. Preferably, the cylindrical element 13 is made of polymeric material or stainless steel. The cylindrical member's central lumen 20 preferably is circular in cross section and has a sufficient diameter to receive different sizes of surgical and diagnostic instruments to be used at an operative site in the body. While in the preferred embodiment, the cylindrical element 13 is tubular with a sufficiently small outer diameter capable of being inserted through the portal 7, it can also be non-tubular in configuration. The cylindrical element 13 and the housing 18 can be either a single, integral piece or two separate pieces joined together by a suitable means, such as welding.

Disposed inside the cylindrical member 12 is an annular lip structure 22 designed to extend outward from the distal opening 14 of the cylindrical member when the sealing conduit 10 is positioned through the portal 7. As shown in FIGS. 1–4, the annular lip structure 22 may be a separate element attached to the inside surface of the cylindrical member 12 near the distal opening 14. The annular lip structure 22 is a bell- or conical-shaped object with an upper, cylindrical neck portion 23 and lower, circular flange portion 24. The neck portion 23 and flange portion 24 are integrally formed so that outer surface of the annular lip structure 22 gently curves in a concave manner. The annular lip structure 22 is preferably made of polymeric material which is biased to straighten and extend outward to form a bell-shaped object when resting. Also, formed on the flange portion 24 are two sets of outward and inward, radially aligned holes 27A and 27B, respectively. During use, the flat, upper surface 25 is pressed against the inside surface of the surrounding wall adjacent to the portal 7. The flat configuration of upper surface 25 facilitates the formation of a seal between an inside surface of the surrounding wall with the annular lip structure 22 when forcibly pressed together.

As mentioned above and as shown in FIGS. 1–3, the annular lip structure 22 may be a separate element with its upper neck portion 23 being securely attached to the inside surface of the cylindrical element 13 with a suitable adhesive. In FIG. 5, the annular lip structure 22 is integrally formed on one end of the cylindrical element 13. In both embodiments, the outer extending edge 26 of the annular lip structure 22 may be square or slightly beveled so that the annular lip structure 22 may easily extend through the distal opening 14 during use.

The housing 18 is integrally formed or attached near the proximal opening 16 of the cylindrical element 13. Like the cylindrical element 13, it is preferably made of polymer or stainless steel. The housing 18 includes an upper cylindrical segment 19 which has an outer diameter greater than the outer diameter of the cylindrical element 13 which enables the housing 18 to act as a grasping surface during use. The housing 18 includes a central passage 30 formed therein which extends and communicates with the cylindrical member's central lumen 20. The central passage 30 preferably has a circular configuration in cross-section, and coaxially, aligned with the central lumen 20.

An optional valve assembly 47 may be mounted inside the housing 18 which prevents bleeding and outside contaminants from entering the portal 7 via the sealing conduit 10. As shown more clearly in FIGS. 2A and 7, the valve assembly 47 includes a flexible disk 48 with a slit opening 49 formed therein. An outer cap 56 is placed over the housing 18 to close the housing 18 and cover the flexible disk 48. The outer cap 56 has a circular aperture 60 formed therein which allows surgical instruments to be inserted through the housing 18 and the cylindrical member 12 when the penetrating member 72 is removed from the cylindrical member 12. The flexible disk 48 is made of flexible, resilient material, such as silicone rubber, which enables the slit opening 49 to be deformed around a particular shape or size to form a tight seal around instruments of various sizes inserted therethrough. The cap 56 is also removable from the housing 18 so that other flexible disks 48 having different sizes of slit openings 49 may be used in the housing 18 for different types of instruments.

Figure 2A:
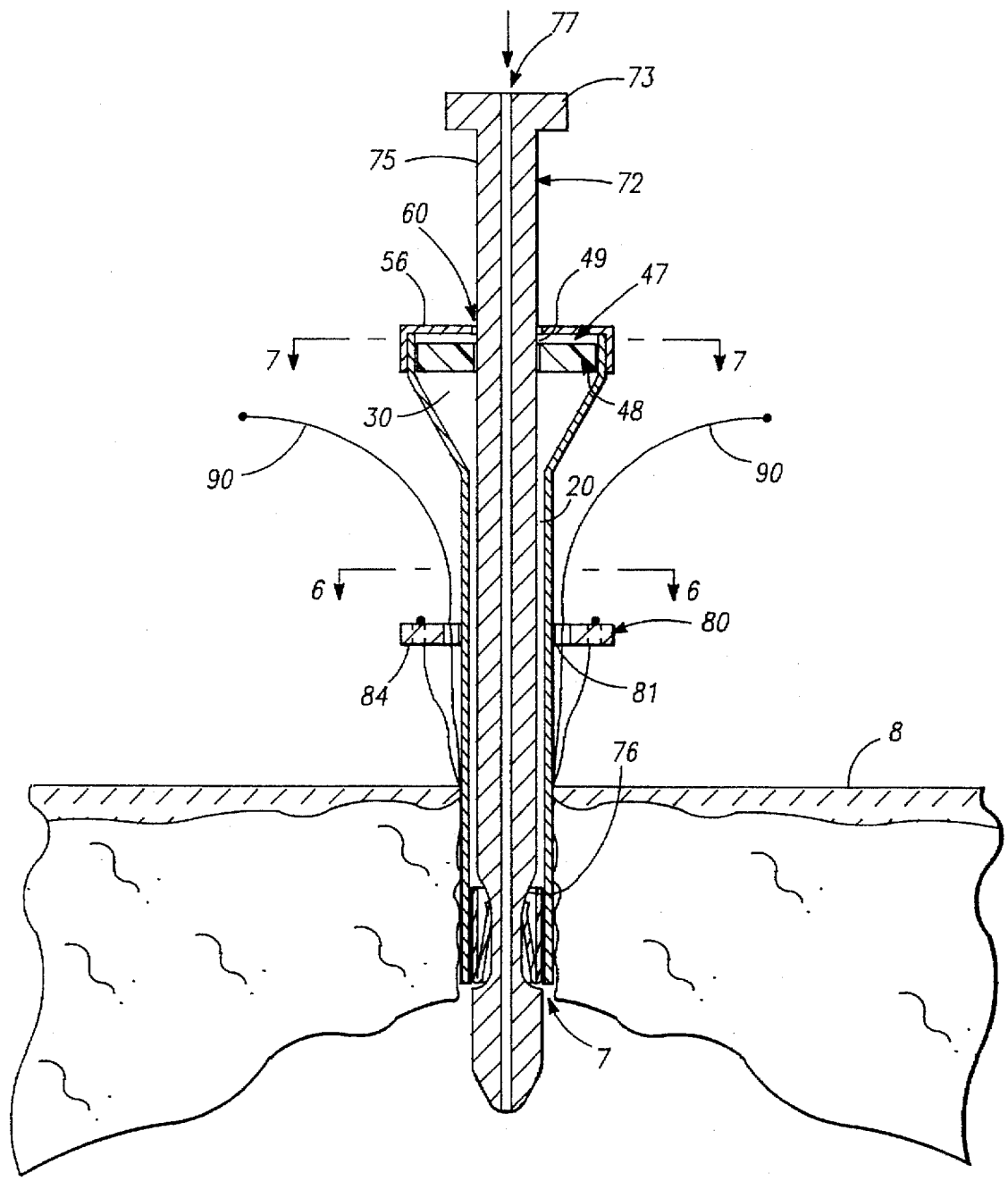
FIG. 2A is a sectional, side elevational view of the sealing conduit being initially inserted through a portal.
Figure 2B:
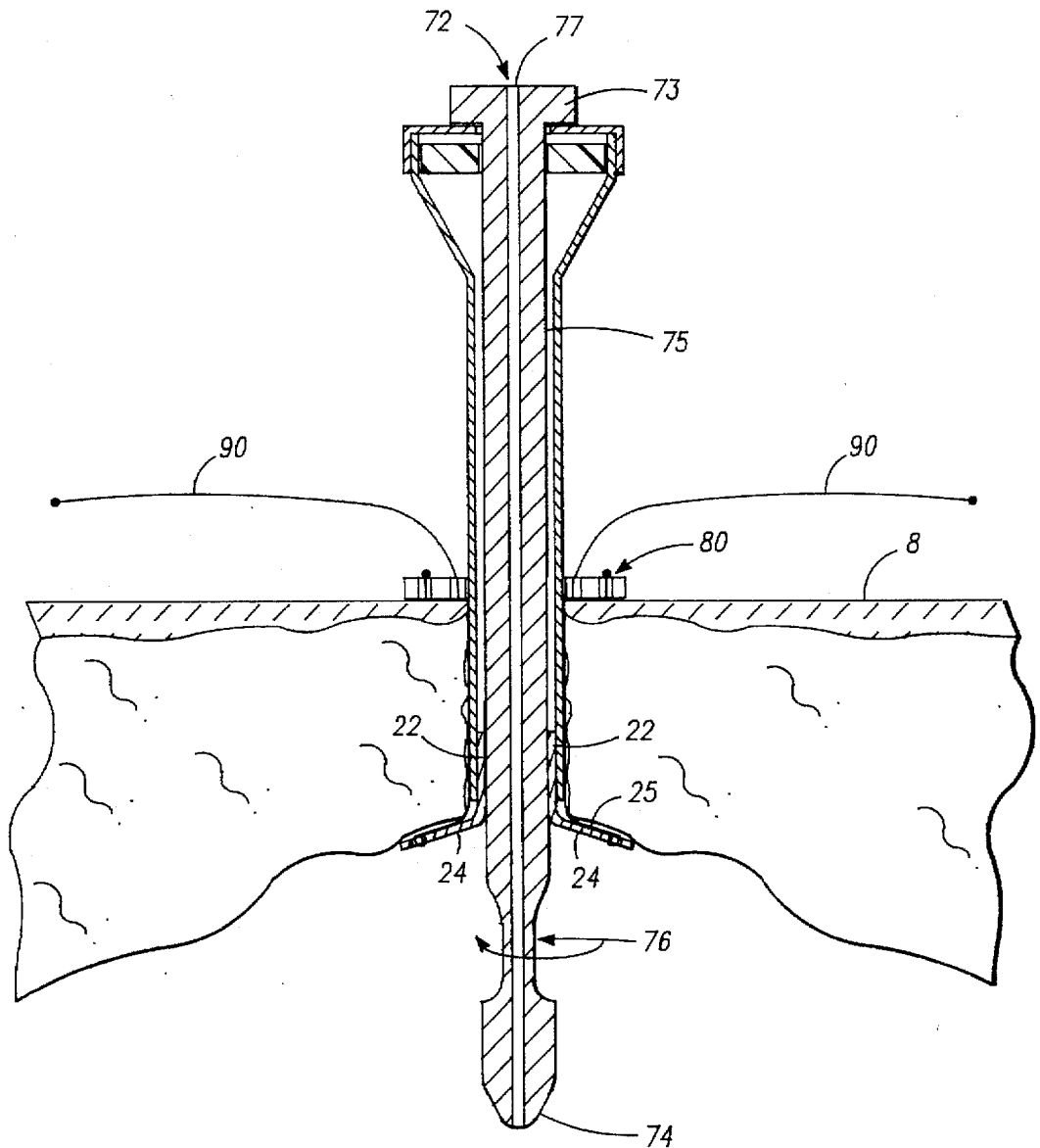
FIG. 2B is a sectional, side elevational view of the sealing conduit similar to the view shown in FIG. 2A showing the penetrating member being moved downward to force the annular lip structure through the distal opening and extended and the upper sealing member being moved downward against the outside surface of the tissue surrounding the portal.
Figure 3:
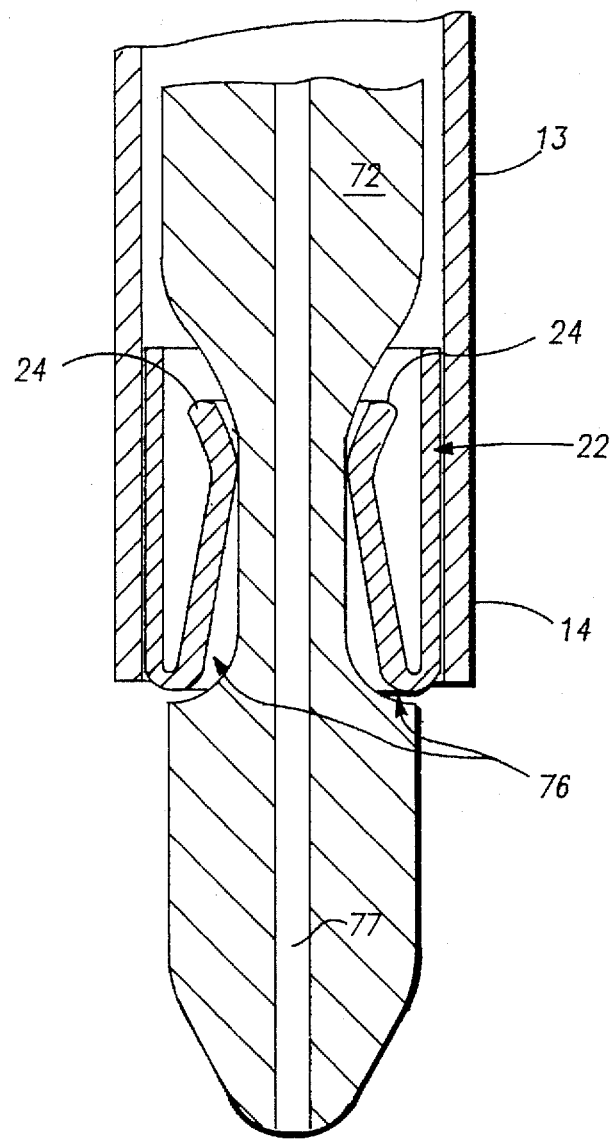
FIG. 3 is a partial, sectional, side elevational view of the sealing conduit showing a separately attached annular lip structure folded in a retracted position inside the cylindrical member.

The sealing conduit 10 also includes a penetrating member 72 which is used to extend the annular lip structure 22 from the cylindrical member 12. As shown in FIGS. 1, 2A, and 2B, the penetrating member 72 is an elongated, cylindrical part 75 with a proximal knob 73, and a relieved area 76 formed thereon located near its distal end. The length of the cylindrical part 75 is sufficient to that the penetrating member 72 extends through the cylindrical member 12. The relieved area 76 is downward sloped to accommodate the flange portion 24 of the annular lip structure 22 when it is folded inside the cylindrical member 12 as shown in FIGS. 3 and 5. The penetrating member 72 is preferably made of a medical grade polymeric material or stainless steel, and has an outer diameter or size that matches the inside diameter of the cylindrical element 13 for a close fit but allowing smooth sliding with minimal required force of penetrating member 72 relative to sealing conduit 10. An optional, longitudinally aligned central hole 77 extends through the penetrating member 72 which is used for passing guide wires (not shown) through the sealing conduit 10 during insertion into the operating site. The distal end 74 of the penetrating member 72 may be a conical-shaped as shown to allow easy penetration into tissue.

Disposed around the cylindrical member 12 is an upper sealing member which is used to create a seal around the cylindrical member and portal during use. In the preferred embodiment, the upper sealing member is a flexible ring 80 which slides upward and downward over the cylindrical member 12. The flexible ring 80 includes a central hole 81 through which the cylindrical member 12 extends. The central hole 81 is sufficient in size so that the flexible ring 80 is tightly formed around the cylindrical member yet allows the flexible ring 80 to move longitudinally upward and downward along the cylindrical member 12 with minimal force.

The flexible ring 80 is preferably made from polymeric, flexible material, such as silicone. The flexible ring 80 has a substantially planar or slightly round lower surface 84 which engages the outer surface of the wall of the tissue surrounding the portal 7 to form seal therearound. Although the flexible ring 80 is shown as being flat in configuration, it will be appreciated that the protrusion can have various other configurations facilitating the formation of a seal between an external surface of a wall or vessel or cavity in the body with the surface of the lower surface 84. The flexible ring 80 can be formed as a single piece or as multiple pieces joined together by known techniques, such as welding or bonding. The flexible ring 80 has an outside and inside set of radially aligned holes 83A, 83B, respectively, which match the spacing and positions of the holes 27A, 27B located on the annular lip structure 22.

The sealing conduit 10 also includes a moving means which the operator uses to selectively move the flexible ring 80 downward over the cylindrical member 12 and against the outside surface of the tissue surrounding the portal 7. In the preferred embodiment, the moving means includes a plurality of suture lines 90 connected at one end to the flexible ring 80 and the annular lip structure 22 to forcibly squeeze them together on opposite sides of the portal 7. Each suture line 90 enters the inside hole 83B on the flexible ring 80 and then extends downward along the outside surface of the cylindrical member 12 to the inside hole 27B on the annular lip structure 22. From the inside hole 27B, it extends laterally and up through the adjacent outside hole 27A and then upward along the outside surface of the cylindrical member 12 to the outside hole 83A located on the flexible ring 80. Each suture line 90 includes multiple strings of flexible with high tensile strength material that is comparable to existing suture material. The first end of each suture line 90 is tied into a knot 91 to prevent it from slipping through hole 83A while the opposite end is left unattached. The length and diameter of the suture lines 90 depends on the size of the conduit used with a general rule of using thicker and longer suture lines with larger diameter conduits. While a multitude of suture lines 90 are used in each sealing conduit 10, the exact number depends on the size of the conduit diameter.

FIGS. 2A and 3 show the sealing conduit 10 with the annular lip structure 22 folded upward into the cylindrical member 12 and retained therein by the relieved area 76 on the penetrating member 72. The flexible ring 80 is mounted on the outside surface of the cylindrical member 12 and multitude of suture lines 90 placed through the holes 83A located thereon in a fashion shown in FIG. 6.

Pulling on the free end of each suture line 90 causes the flexible ring 80 to move downward longitudinally along the outside surface of the cylindrical member 12 toward the annular lip structure 22. The sealing conduit 10 preferably would be supplied pre-assembled and ready for use and would not require the above mentioned steps of suture lines 90 placement through the flange holes 83 and the annular lip structure holes 23.

The exact configuration and dimensions for the sealing conduit 10 can vary in size from 1 to 27 mm. The outer diameter of the cylindrical member 12, the outer diameter of the flexible ring 80, the distance between the distal end 14 to the flexible ring 80, the width of the flange portion 24 of the annular lip structure 22, and the diameter of the central lumen 20 can vary for specific applications.

To use the sealing conduit 10, a portal 7 of minimal size, is first formed in tissue 8 as shown in FIGS. 1, 2A and 2B.

Once the portal 7 is formed, a clamping device (not shown) can be used to isolate a section of the cavity or vessel for conduit insertion. Once the portal 7 is isolated, the sealing conduit 10 is then inserted through the portal 7 such that the distal end 14 of the cylindrical member 12 is disposed in the body as shown in FIG. 2A. During insertion of the sealing conduit 10 through the tissue 8, the optional tapered end 78 of the penetrating member 72 facilitates insertion of the sealing conduit 10 through the portal 7. After being placed through the portal 7, the penetrating member 72 is advanced relative to the cylindrical member 12 to force the annular lip structure 22 out of the cylindrical member 12 and into the cavity or vessel lumen as shown in FIG. 2B. Next, the free ends of the suture lines 90 are pulled simultaneously to force the flexible disk 82 downward over the cylindrical member 12 towards the annular lip structure 22. While the suture lines are being pulled, the surrounding tissue 8 can be manipulated or spread to facilitate the advancement of the flexible ring 80 over the cylindrical member 12. Once the bottom surface of the flexible ring 80 makes contact with the outside surface of the cavity or vessel, as shown in FIG. 2B, any additional pulling on the free ends will force the flexible ring 80 and the annular lip structure 22 together form a seal therebetween. The ends of the suture lines 90 are then tied together or secured in a suitable manner to hold the flexible ring 80 and annular lip structure 22 in place.

The annular lip structure 22 is positioned against the inside surface by engagement of the upper surface 25 therewith to prevent the cylindrical member 12 from backing out from the portal 7. With the annular lip structure 22 pressed against the inside surface, the distal end 14 of the sealing conduit 10 protrudes from the inside surface a short distance such that contact with and possible damage to anatomic structure within the body or affecting fluid flow inside a vessel is avoided. The penetrating member 72 is then removed from the cylindrical member 12. A surgical instrument selected in accordance with the surgical procedure to be performed at the operative site is introduced through the sealing conduit 10, the surgical instrument extending through the outer cap 56, the valve assembly 48 and the central lumen 20 of the sealing conduit 10 and exiting the distal end 14 for positioning at the operative site. Upon completion of the procedure to be performed by the instrument, the instrument is withdrawn from the operative site through the central lumen 20 of the sealing conduit 10, and various other diverse sizes and types of instruments can be introduced at the operative site via the lumen of the conduit 10.

Figure 6:
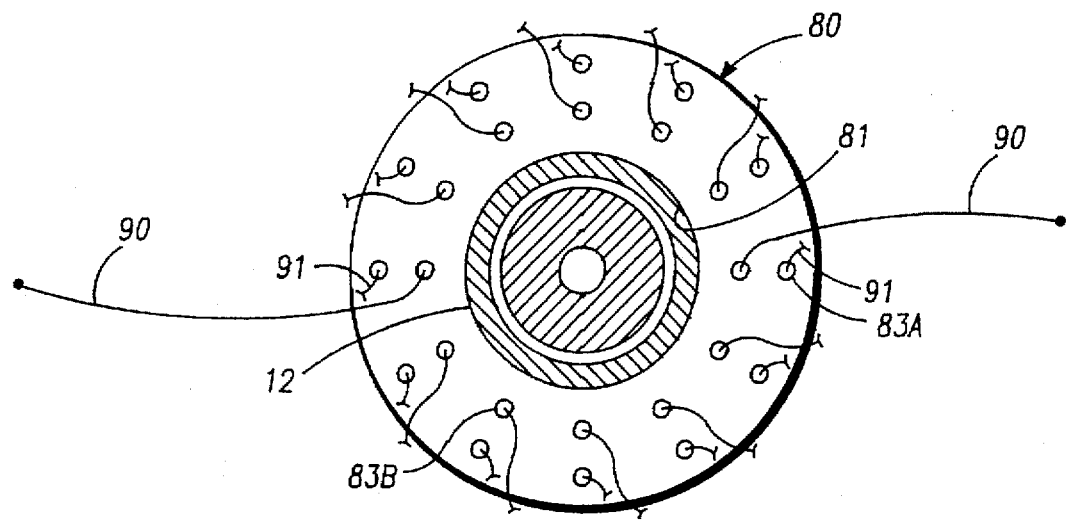
FIG. 6 is a sectional view taken along line 6—6 in FIG. 2A.
Figure 7:
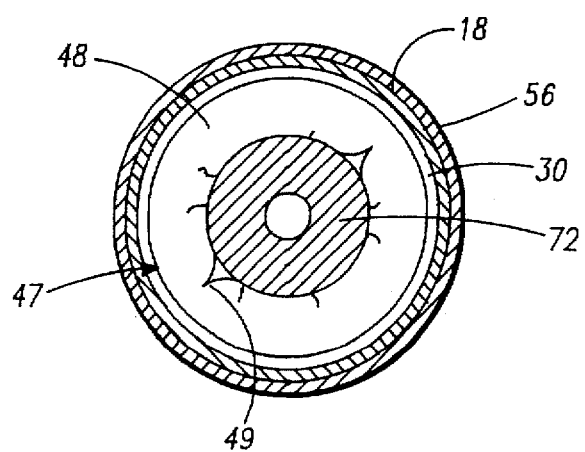
FIG. 7 is a sectional view taken along line 7—7 in FIG. 2A.

Once the surgical procedure has been completed, a clamping device may be used to isolate the section of the cavity or vessel where the sealing conduit 10 has been inserted as shown in FIG. 6. Once the cavity or vessel is isolated, the suture lines 90 are then loosened so that the annular lip structure 22 can be bent inward to allow the sealing conduit 10 to be manually withdrawn from the portal. Before completely withdrawing the sealing conduit 10, a stapling or suturing device could be introduced through the sealing conduit 10 to close the incision left behind by the sealing conduit 10.

It will be appreciated that the sealing conduit 10 can be inserted in the body after the portal has been formed in the wall with the penetrating instrument or that the sealing conduit 10 can be inserted during formation of the portal by mounting the penetrating instrument in the lumen of the conduit such that the conduit moves through the tissue along with the penetrating instrument allowing the penetrating instrument to be removed from the conduit leaving the sealing conduit 10 in place.

The sealing conduit 10 of the present invention is useful in various types of surgery procedures to provide access to operative sites in the body via small size portals allowing surgical instruments to be introduced at the operative sites through the sealing conduit 10 with the sealing conduit 10 being prevented from backing out or protruding from the body until surgical or diagnostic procedures have been completed and the sealing conduit 10 is intentionally withdrawn.

The sealing conduit 10 is particularly useful in procedures requiring vessel or heart chamber access, such as angioplasty, least invasive bypass surgery, least invasive valve repair and cardiac support, where a blood pump is placed through the conduit to unload the heart partially or completely, where portals formed in tissue adjacent to the heart and it major vasculators. According to a method of operation for the sealing conduit 10 in introducing surgical instruments in angioplasty procedures, least invasive bypass surgery, least invasive valve repair and cardiac support, where a blood pump is placed through the conduit to unload heart partially or completely where portals formed in tissue adjacent to the heart and it major vasculators with the heart and it's vasculators being visualized with an arthroscope. The sealing conduit 10 is inserted through the chest such that the distal end 14 is disposed within the body, and the upper surface 25 of the annular lip structure 22 is positioned against an internal surface from the heart chamber or vasculators. With the annular lip 22 engaging the internal surface of the tissue, the distal opening 14 protrudes from the internal surface only a short distance such that the flow is not affected. Surgical instruments selected in accordance with the procedure to be performed are introduced at the heart or its vasculators through the sealing conduit 10 with the sealing conduit 10 providing a smooth passage for introducing the surgical instruments at the heart or its vasculators through the relatively thick tissue while preventing extravasation. Upon completion of the surgical procedure and removal of the surgical instruments, the sealing conduit 10 is withdrawn from the tissue of the heart or its vasculators and the portal is closed.

Accordingly, the sealing conduit 10 and methods of introducing surgical instruments at operative sites in the body in surgical and diagnostic procedures facilitate various surgical and diagnostic procedure and, in particular, arthroscope procedures such as angioplasty, least invasive bypass surgery, least invasive valve repair and cardiac support, where a blood pump is placed through the conduit to unload heart partially or completely where portals formed in tissue adjacent to the heart and it's major vasculators, prevent extravasation when introducing surgical instruments at operative sites in the body via portals of minimal size, allow the sealing conduit 10 to be anchored relative to a wall of the body while protruding into the body only a short distance, facilitate insertion through tissue of an anatomical wall, provide smooth passage for introducing surgical instruments through portals in tissue of anatomical walls and, in particular walls having relatively great thicknesses, allow various sizes and types of surgical instruments to be introduced via the lumen of the sealing conduit 10 with the sealing conduit 10 being inserted through a portal just large enough to accommodate the sealing conduit 10, avoid inadvertent contact with anatomic structure in the body and prevent withdrawal of the sealing conduit 10 from the body except upon completion of the surgical procedure when the conduit can be intentionally withdrawn.

In compliance with the statute, the invention, described herein, has been described in language more or less specific as to structural features. It should be understood, however, the invention is not limited to the specific features shown, since means and construction shown comprised only the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. A sealing member, comprising:
   a. a cylindrical member, said cylindrical member having a distal end and a proximal end with a continuous, longitudinally aligned central lumen formed therein;
   b. an annular lip structure formed on said distal end of said cylindrical member, said annular lip structure capable of being disposed between a retracted position inside said cylindrical member and an extended position on said distal end of said cylindrical member, said annular lip structure capable of preventing the outward migration of said cylindrical member in a portal when said cylindrical member is inserted therein and said annular lip structure is extended from said cylindrical member;
   c. a removable penetrating member longitudinally disposed inside said cylindrical member, said penetrating member capable of supporting said cylindrical member when said cylindrical member is inserted into a portal said penetrating member being an elongated structure with a distal end and a relieved area formed adjacent thereto said relieved area having an ohter shape and being located on said penetrating member so that said annular lip structure may be disposed in a retracted position inside said cylindrical member within said relieved area when said penetrating member is disposed inside said cylindrical member, said penetrating member also being sufficient size so that said annular lip structure disposed inside said cylindrical member may be forcibly moved outward from said cylindrical member when said penetrating member is moved longitudinally downward inside said cylindrical member,
   d. An upper sealing member capable of moving downward longitudinally along said cylindrical member and pressed against the outside surface of the tissue surrounding a portal formed therein, said upper sealing member capable of sealing said portal and preventing the inward migration of said cylindrical member through the portal; and,
   e. A moving means capable of selectively moving said annular lip structure from a restricted position to an extended position from said cylindrical member, said moving means also capable of moving said upper sealing member along said cylindrical member to force said upper sealing member and said annular lip structure together to securely hold and form a seal around said portal.

2. A sealing conduit, as recited in claim 1, wherein said upper sealing member is a flexible disk having a central bore formed therein, said central bore being complimentary in shape and size with said cylindrical body so that said flexible disk may selectively move longitudinally along said cylindrical member.

3. A sealing conduit, as recited in claim 2, wherein said moving means is a plurality of suture lines disposed between said annular lip structure and said upper sealing means, each said suture line being connected between said annular lip structure and said upper sealing means so that when said suture lines are pulled, said upper sealing means is moved longitudinally along said cylindrical member to force said upper sealing means and said annular lip structure against the tissue surrounding said portal.

4. A sealing member, as recited in claim 1, further including a valve member attached to said cylindrical member, said valve member capable of sealing said central lumen in said cylindrical member and enabling said penetrating member to move longitudinally inside said cylindrical member.

5. A sealing conduit, as recited in claim 4, wherein said valve member is a replaceable flat disk with a slit opening formed therein, said slit opening having a size and shape complimentary to the outside size and shape of an instrument inserted through said cylindrical member to form a seal therearound.

6. Method of attaching a conduit to a portal formed in anatomical tissue, comprising the following steps:
   a. selecting a sealing conduit, said sealing conduit includes a cylindrical member with a retractable and extendable, outward biased, annular lip structure, a penetrating member, disposed inside said cylindrical member, said penetrating member being an elongated structure with a distal end and a relieved area formed adjacent thereto, said relieved area having an outer shape and being located on said penetrating member so that said annular lip structure may be disposed in a retracted position inside said cylindrical member within said relieved area when said penetrating member is disposed inside said cylindrical member, said penetrating member also being sufficient size so that said annular lip structure disposed inside said cylindrical member may be forcibly moved outward from said cylindrical member when said penetrating member is moved longitudinally downward inside said cylindrical member, an upper sailing means capable of being moved longitudinally over said cylindrical member, and a moving means for forcibly moving said upper sealing means along said cylindrical member and forcing said upper sealing means and said annular lip structure together on opposite sides of the portal to hold said cylindrical member in position in the portal and to create a seal therearound during use;
   b. inserting said sealing conduit through a portal;
   c. using said moving means to force said annular lip structure and said upper sealing means together to securely hold said sealing conduit in the portal and to create a seal therearound; and,
   d. removing said penetrating member from said cylindrical member to provide access through the portal.

* * * * *